(12) United States Patent
Jungles et al.

(10) Patent No.: US 7,566,462 B2
(45) Date of Patent: Jul. 28, 2009

(54) STABLE TABLET FORMULATION

(75) Inventors: Steven Jungles, Novato, CA (US); Mark A. Henderson, Larkspur, CA (US); Victoria Sluzky, Corte Madera, CA (US); Robert Baffi, Moraga, CA (US)

(73) Assignee: BioMarin Pharmaceutical Inc., Novato, CA (US)

( * ) Notice: Subject to any disclaimer, the term of this patent is extended or adjusted under 35 U.S.C. 154(b) by 0 days.

(21) Appl. No.: 12/106,621

(22) Filed: Apr. 21, 2008

(65) Prior Publication Data

US 2008/0207626 A1   Aug. 28, 2008

Related U.S. Application Data

(63) Continuation of application No. 10/563,418, filed as application No. PCT/US2005/041252 on Nov. 16, 2005.

(60) Provisional application No. 60/629,189, filed on Nov. 17, 2004.

(51) Int. Cl.
    *A61K 9/20*   (2006.01)
(52) U.S. Cl. .................................. 424/464; 424/465
(58) Field of Classification Search .................. 424/464, 424/465
    See application file for complete search history.

(56) References Cited

U.S. PATENT DOCUMENTS

| | | | |
|---|---|---|---|
| 4,778,794 A | 10/1988 | Naruse et al. | |
| 5,753,656 A | 5/1998 | Sakai et al. | |
| 6,288,067 B1 | 9/2001 | Okamura et al. | |
| 6,410,535 B1 | 6/2002 | Kashiwagi et al. | |
| 6,417,205 B1 | 7/2002 | Cooke et al. | |
| 2004/0058896 A1* | 3/2004 | Dietrich et al. | ............. 514/171 |
| 2006/0035900 A1 | 2/2006 | Moser et al. | |
| 2006/0040946 A1 | 2/2006 | Oppenheimer et al. | |
| 2008/0207624 A1 | 8/2008 | Sugita et al. | |

FOREIGN PATENT DOCUMENTS

| | | |
|---|---|---|
| EP | 1757293 A1 | 2/2007 |
| WO | WO 2005/107759 | 11/2005 |
| WO | WO 2006/063215 | 6/2006 |
| WO | WO 2007/067570 | 6/2007 |

OTHER PUBLICATIONS

FDA Center for Drug Evaluation and Research (CDER) Draft Guidance for Industry ANDAs: Pharmaceutical Solid Polymorphism Chemistry, Manufacturing, and Controls Information, dated Dec. 2004.
Schirck's Laboratories "Summary of Product Characteristics—Tetrahydrobiopterin 10 mg/50 mg Tablets," dated Jan. 7, 2004.
Written Opinion for corresponding International Application PCT/US05/041252, dated Aug. 11, 2006.
"Tetrahydrobiopterin tablets" by Schircks Laboratories, Aug. 15, 2003.
" Data Sheet—Tetrahydrobiopterin" by Schircks Laboratories, Sep. 16, 2003.
"Certificate of Analysis" by Schircks Laboratories, Mar. 11, 2005.
"Tetrahydrobiopterin tablets" by Schircks Laboratories, Jan. 8, 2008.
"Statement for the Record" from the file history of U.S. Appl. No. 10/990,316, Feb. 25, 2008.
"Summary of product characteristics—Tetrahydrobiopterin tablets" by Schircks Laboratories, Mar. 31, 2008.

* cited by examiner

*Primary Examiner*—Michael G. Hartley
*Assistant Examiner*—James W. Rogers
(74) *Attorney, Agent, or Firm*—Jones Day (57) ABSTRACT

The present invention is directed to a stable solid formulations of tetrahydrobiopterin, processes for producing them, and treatment methods using such formulations.

20 Claims, 1 Drawing Sheet

FIGURE 1

STABLE TABLET FORMULATION

CROSS REFERENCE TO RELATED APPLICATIONS

This application is a continuation of U.S. Ser. No. 10/563,418, which is a national stage application of International Application No. PCT/US05/41252, filed Nov. 16, 2005, which claims the benefit of U.S. Provisional Application No. 60/629,189, filed Nov. 17, 2004, the entirety of each is incorporated herein by reference.

NAMES OF PARTIES TO A JOINT RESEARCH AGREEMENT

BioMarin Pharmaceutical Inc. and Merck Eprova AG

BACKGROUND

1. Field

The present invention is generally directed to stable tablet formulations of tetrahydrobiopterin or precursors, derivatives or analogs thereof for the treatment of humans.

2. Background of the Related Technology

Tetrahydrobiopterin (sometimes referred to as BH4) is a biogenic amine of the naturally-occurring pterin family that is a cofactor for a number of different enzymes, including phenylalanine hydroxylase (PAH), tyrosine hydroxylase, tryptophan hydroxylase and nitric oxide synthase. Pterins are present in physiological fluids and tissues in reduced and oxidized forms, however, only the 5,6,7,8, tetrahydrobiopterin is biologically active. It is a chiral molecule and the 6R enantiomer of the cofactor is known to be the biologically active enantiomer. For a detailed review of the synthesis and disorders of BH4 see Blau et al., 2001 (*Disorders of tetrahydrobiopterin and related biogenic amines*. In: Scriver C R, Beaudet A L, Sly W S, Valle D, Childs B, Vogelstein B, eds. The Metabolic and Molecular Bases of Inherited Disease. 8th ed. New York: McGraw-Hill, 2001: 1275-1776).

A deficiency in PAH activity, due to absent or mutated PAH enzyme or a deficiency in its cofactor BH4, manifests as an excess of the amino acid phenylalanine (Phe) known as hyperphenylalaninemia (HPA) in its very mildest forms or phenylketonuria (PKU) in its moderate or severe forms. PAH deficiency also causes a deficiency in the amino acid tyrosine, which is a precursor for synthesis of neurotransmitters. A deficiency in tyrosine hydroxylase or tryptophan hydroxylase activity can manifest as a deficiency in neurotransmitter production.

Despite the elucidation of the role of BH4 deficiency in phenylketonuria, treatment with BH4 has not been suggested because such treatment is very expensive, as high as $30,000 per year for an adolescent or adult, as compared with $6,000 for phenylalanine-restricted dietary therapy (Hanley, N. *Engl. J. Med* 348(17):1723, 2003). Another significant problem with BH4 is that this compound is unstable and readily undergoes aerobic oxidation at room temperature (Davis et al., *Eur. J. Biochem.*, Vol 173, 345-351, 1988; U.S. Pat. No. 4,701,455) and has a shelf-life of less 8 hours at room temperature (Berneggar and Blau, *Mol. Genet. Metabol.* 77:304-313, 2002).

Other tetrahydrobiopterin products available on the market need to be specially packaged or kept frozen. For example the labeling on the tablets sold by Schirck's Laboratory specify that the tablets should be kept frozen and state that the product has a shelf life at room temperature of only 2 months. BIOPTEN (tetrahydrobiopterin granules) requires expensive, hermetically-sealed foil packaging to maintain room temperature stability. The instability of such BH4 compositions is commercially undesirable and significant degradation due to improper storage could hinder therapy of patients.

Drug substance polymorphic forms can exhibit different physical and mechanical properties, including hygroscopicity, particle shape, density, flowability, and compactability, which in turn may affect processing of the drug substance and/or manufacturing of the drug product. The effect of polymorphism on pharmaceutical processing also depends on the formulation and the manufacturing process. Polymorphic forms of the drug substance can undergo phase conversion when exposed to a range of manufacturing processes, such as drying, milling, micronization, wet granulation, spray-drying, and compaction. Exposure to environmental conditions such as humidity and temperature can also induce polymorph conversion. The extent of conversion generally depends on the relative stability of the polymorphs, kinetic barriers for phase conversion, and applied stress. See FDA Center for Drug Evaluation and Research (CDER) Draft Guidance for Industry ANDAs: Pharmaceutical Solid Polymorphism Chemistry, Manufacturing, and Controls Information, December 2004.

Thus, there remains a need for a stable solid formulation of tetrahydrobiopterin and processes for manufacturing such stable formulations. The present invention is directed to addressing such a need.

SUMMARY OF THE INVENTION

The present invention relates to stable solid formulations of tetrahydrobiopterin, particularly stable tablets, processes for producing such formulations, and treatment methods using such formulations.

The invention provides a stable solid formulation of tetrahydrobiopterin, or a precursor or derivative or analog thereof, that maintains its stability for an extended period of time. Compositions of the invention may comprise a stable, crystalline form of BH4 that is stable at room temperature for more than 8 hours and a pharmaceutically acceptable carrier, diluent or excipient. Exemplary stable tablets of the invention have been prepared using a dry tableting process and have been shown to have a shelf-life of at least 6 to 9 months at room temperature.

Another aspect of the invention provides a dry formulation process for preparing stable solid formulations, which includes the step of mixing tetrahydrobiopterin, or a precursor or derivative or analog thereof, with another pharmaceutical carrier, diluent or excipient, in the absence of added water.

In an exemplary embodiment, the active pharmaceutical ingredient and excipients are dry blended and compressed. The tablets are processed in humidity-controlled rooms where humidity is kept at about 65% (±5%) or less. Once processed, the tablets are stored in triple plastic lined water resistant containers with desiccant pillows lined between the outer two layers of plastic bags. Thus, the invention includes a dry formulation method comprising the steps of mixing an initial amount of a crystalline polymorph of (6R)-L-erythro-tetrahydrobiopterin, preferably polymorph B, and one or more pharmaceutically acceptable excipients, and forming a tablet from the mixture, wherein the steps do not include adding liquid water. Exemplary particle sizes include, e.g., from about 0.2 μm to about 500 μm, from about 1 μm to about 250 μm, or from about 2 μm to about 200 μm, or, e.g., smaller than about 500 µm, smaller than about 600 µm, smaller than about 700 µm, or smaller than about 850 µm.

In exemplary embodiments, the tablet is initially manufactured using a stable crystalline form of (6R)-5,6,7,8-tetrahydrobiopterin described below as "polymorph B," and retains at least about 95% of the active pharmaceutical ingredient (API) at room temperature after 3 months, 6 months or 9 months, or preferably 12 months or longer, e.g. 15 months, 18 months, 21 months, 2 years, 2.5 years, 3 years or longer. Preferably the tablet retains at least about 90%, 91%, 92%, 93%, 94%, 95%, 96%, 97%, 98%, 99%, or 99.5% of the API after storage at room temperature for such time periods. The tablet also preferably exhibits loss on drying of 2% or less, or 1.5% or less, or 1% or less, or 0.9% or less, or 0.8% or less, or 0.7% or less, or 0.6% or less, after such time periods. Exemplary tablets may be manufactured wherein the initial amount of tetrahydrobiopterin active pharmaceutical ingredient is about 25 mg, 50 mg, 75 mg, 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg or higher doses. Preferred tablets also exhibit rapid disintegration upon administration, e.g., 3 minutes or less, to improve ease of administration.

Thus, the invention provides a stable tablet formulation comprising an initial amount of a crystalline polymorph, designated polymorph B, of (6R)-L-erythro-tetrahydrobiopterin and a pharmaceutically acceptable excipient, wherein after six months at room temperature and about 60% humidity the stable tablet formulation retains at least about 95% of the initial amount of (6R)-L-erythro-tetrahydrobiopterin, and wherein said crystalline polymorph, as a hydrochloride salt, exhibits an X-ray powder diffraction pattern with the following characteristic peaks expressed in d-values (A): 8.7 (vs), 5.63 (m), 4.76 (m), 4.40 (m), 4.00 (s), 3.23 (s), 3.11 (vs), preferably 8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), and 2.44 (w). Preferably the tablet retains at least about 90%, 91%, 92%, 93%, 94%, 95%, 96%, 97%, 98%, 99%, or 99.5% of the initial amount of (6R)-L-erythro-tetrahydrobiopterin.

The stable solid formulation preferably contains one or more of the following additional ingredients that improve stability or other characteristics of the formulation: binder, disintegrant, acidic antioxidant, or lubricant or combinations thereof. One exemplary preferred composition includes anhydrous dibasic calcium phosphate, crospovidone, ascorbic acid and stearyl fumarate, optionally with mannitol and riboflavin. The stable solid formulation may optionally include other therapeutic agents suitable for the condition to be treated, e.g. folates, including folate precursors, folic acids, or folate derivatives; and/or vitamins such as vitamin C and/or vitamin B12; and/or neurotransmitter precursors such as L-dopa or carbidopa; and/or 5-hydroxytryptophan; and/or arginine. Compositions comprising tetrahydrobiopterin (or a precursor or derivative or analog) and a folate, and optionally further comprising arginine, are particularly contemplated.

The invention further contemplates other stable solid formulations for oral administration, e.g. capsules, pills or troches, with similar stability properties.

Yet another aspect of the invention provides treatment methods using such stable solid formulations. The invention contemplates that such formulations of the invention are useful for intervention in metabolic disorders, particularly those involving amino acid metabolism. More particularly, the stable formulations may be used for the treatment of subjects exhibiting elevated phenylalanine levels or decreased tyrosine levels, for example, subjects suffering from hyperphenylalanemia, mild phenylketonuria or classic severe phenylketonuria; and for the treatment of subjects suffering from conditions that would benefit from enhancement of nitric oxide synthase activity, including vascular diseases, ischemic or inflammatory diseases, diabetes, or insulin resistance. The total dose required for each treatment may be administered in multiple doses or in a single dose. The stable formulations may be administered daily or at some other interval, e.g., every alternative day or even weekly.

The stable formulations may be used alone or in conjunction with other therapies suitable for the disorder to be treated, including the underlying disease or the clinical symptoms. For example, for HPA, the stable formulations of the invention may be administered in combination with a protein-restricted diet, e.g. where the subject is limited to about 600 mg or less, or about 300 mg or less of protein daily, optionally with supplemental amino acids, such as tyrosine, valine, isoleucine and leucine. The stable formulations may also be administered in combination with folates, arginine, vitamins, or neurotransmitter precursors. As another example, for vascular diseases, diabetes, or insulin resistance, the stable formulations of the invention may be administered in conjunction with other therapeutic agents such as anti-hypertensive agents, anti-platelet agents, cholesterol-lowering agents, insulin or oral hypoglycemic agents.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

DESCRIPTION OF THE PREFERRED EMBODIMENTS

The present invention provides a stable formulation that maintains a stable crystalline polymorph of the active ingredient. An anhydrous polymorph of (6R)-5,6,7,8-tetrahydrobiopterin dihydrochloride that is stable at room temperature to atmospheric oxygen and normal humidity, described below as polymorph B, has been identified. However, when the percent relative humidity approaches 80%, polymorph B appears to take up much more water, loses its crystalline form, and becomes labile to oxidation.

By using a dry formulation process, the stable crystalline structure of this polymorph is maintained in the finished product. In contrast, other processes for preparing tetrahydrobiopterin compositions result in a less stable product compared to those of the present invention.

Stable tablet formulations of the invention have been made using polymorph B in a dry formulation process and have been shown to retain 99% or more of the initial (6R)-5,6,7,8-tetrahydrobiopterin for at least 6 or 9 months, both at normal room temperature and humidity, and under accelerated testing conditions. The observed stability under accelerated testing conditions, i.e. higher temperature and humidity, indicates that the tablet formulations would be stable for far longer than 6 or 9 months at normal room temperature and humidity.

As used herein, "shelf life" means the storage period during which an active pharmaceutical ingredient (API) in a pharmaceutical formulation has minimal degradation (e.g., not more than about 5% degradation) when the pharmaceutical formulation is stored under specified storage conditions, for example, room temperature at normal humidity.

The shelf-life of the stable formulations of the invention may be measured as follows. The formulation to be tested may be divided into one or more different batches and stored under typical storage conditions, for example, 4° C. (refrigerator), or 25° C. (room temperature). Degradation of the API in a pharmaceutical formulation can also be detected using accelerated testing under exaggerated storage conditions designed to increase the degradation rate of the drug substance. For example, a batch can be "stressed" (placed in chamber which maintains a temperature of 45° C. and 75% humidity). Samples of each batch of formulation are then analyzed at different time points (e.g., time zero, 2 weeks, 1 month, 3 months, 6 months, 9 months, 1 year, 1.5 years, 2 years, 2.5 years, 3 years or longer) for amount of API still present in the formulation. Analysis of the API in the formulation may be carried out by a variety of detection methods including high performance liquid chromatography, crystal or powder X-ray diffraction, infrared or Raman spectra studies, microscopy, differential scanning calorimetry, thermal gravimetric analysis, hot-stage microscopy, and solid state nuclear magnetic resonance. Maintenance of a particular polymorph form can be determined by carrying out, e.g., powder or crystal X-ray diffraction studies or any of the same techniques used to analyze the polymorph initially.

I. SYNTHESIS OF TETRAHYDROBIOPTERIN, PRECURSORS, DERIVATIVES AND ANALOGS

A variety of methods are known in the art for synthesis of tetrahydrobiopterins, precursors, derivatives and analogs. U.S. Pat. Nos. 5,698,408; 2,601,215; 3,505,329; 4,540,783; 4,550,109; 4,587,340; 4,595,752; 4,649,197; 4,665,182; 4,701,455; 4,713,454; 4,937,342; 5,037,981; 5,198,547; 5,350,851; 5,401,844; 5,698,408, Canadian application CA 2420374, European application nos. EP 079 574, EP 191 335 and Suntory Japanese patent publications JP 4-082888, JP 59-021685 and JP 9-157270, as well as Sugimoto and Matsuura, *Bull. Chem. Soc. Japan,* 48(12):3767-3768 (1975), Sugimoto and Matsuura, *Bull. Chem. Soc. Japan,* 52(1):181-183 (1979), Matsuura et al., Chem. Lett. (Japan), 735-738 (1984), Matsuura et al., *Heterocycles,* Vol. 23, No. 12, 3115-3120, 1985 and Whiteley et al., *Anal Biochem.* 137(2):394-6 (1984) (each incorporated herein by reference) each describe methods of making dihydrobiopterins, BH4 and derivatives thereof that may be used as compositions for the present invention.

Int'l Publication No. WO2005049614, U.S. Pat. No. 4,540,783, Japanese Patent No. 59-021685, Schircks et al., *Helv. Chim. Acta,* 60: 211 (1977), Sugimoto et al., *Bull. Chem. Soc. Jp,* 52(1):181 (1979), Sugimoto et al., *Bull. Chem. Soc. Jp,* 48(12):3767 (1975), Visontini et al., *Helv. Chim. Acta,* 52:1225 (1969), and Matsuura et al., *Chem. Lett.,* p 735 (1984), incorporated herein by reference in their entireties, describe methods of synthesizing BH4.

Nonlimiting examples of analogs for use in the compositions and methods described herein include pteridine, pterin, neopterin, biopterin, 7,8-Dihydrobiopterin, 6-methyltetrahydropterin, and other 6-substituted tetrahydropterin and other 6-substituted tetrahydropterins, sepiapterin, 6,7-Dimethyltetrahydropterin, 6-methyl biopterin and other 6-substituted biopterins, and other analogs that are described in the art. Nonlimiting examples of derivatives for use in the compositions and methods described herein include the derivatives described in U.S. Pat. Nos. 4,758,571; 4,774,244; 6,162,806; 5,902,810; 2,955,110; 2,541,717; 2,603,643; and 4,371,514, the disclosures of which are hereby incorporated herein.

Any such methods or other methods known in the art may be used to produce BH4, or precursors, derivatives or analogs for use in the stable formulations and therapeutic methods of the present invention.

II. CRYSTAL POLYMORPHS OF 6R-TETRAHYDROBIOPTERIN HYDROCHLORIDE SALT

It has been found that BH4, and in particular, the dihydrochloride salt of BH4, exhibits crystal polymorphism. The structure of BH4 is shown below:

The (6R) form of BH4 is the known biologically active form, however, BH4 is known to be unstable at ambient temperatures.

BH4 is difficult to handle and it was therefore produced and offered as its dihydrochloride salt (Schircks Laboratories, Jona, Switzerland) in ampoules sealed under nitrogen to prevent degradation of the substance due to its hygroscopic nature and sensitivity to oxidation. U.S. Pat. No. 4,649,197 discloses that separation of (6R)- and 6(S)-L-erythro-tetrahydrobiopterin dihydrochloride into its diastereomers is difficult due to the poor crystallinity of 6(R,S)-L-erythro-tetrahydrobiopterin dihydrochloride. The European patent number 0 079 574 describes the preparation of tetrahydrobiopterin, wherein a solid tetrahydrobiopterin dihydrochloride is obtained as an intermediate. S. Matsuura et al. describes in Chemistry Letters 1984, pages 735-738 and Heterocycles, Vol. 23, No. 12, 1985 pages 3115-3120 6(R)-tetrahydrobiopterin dihydrochloride as a crystalline solid in form of colorless needles, which are characterized by X-ray analysis disclosed in J. Biochem. 98, 1341-1348 (1985). An optical rotation of 6.81° was found the crystalline product, which is quite similar to the optical rotation of 6.51° reported for a crystalline solid in form of white crystals in example 6 of EP-A2-0 191 335.

Results obtained during development of (6R)-L-erythro-tetrahydrobiopterin dihydrochloride indicated that the compound may exist in different crystalline forms, including polymorphic forms and solvates. It has been found that one crystal polymorph of BH4 is more stable, and is stable to decomposition under ambient conditions.

Polymorph Form B

The crystal polymorph that has been found to be the most stable is referred to herein as "form B," or alternatively as "polymorph B."

Polymorph B is a slightly hygroscopic anhydrate with the highest thermodynamic stability above about 20° C. Further-more, form B can be easily processed and handled due to its thermal stability, possibility for preparation by targeted conditions, its suitable morphology and particle size. Melting point is near 260° C. (ΔHf>140 J/g), but no clear melting point can be detected due to decomposition prior and during melting. These outstanding properties renders polymorph form B especially feasible for pharmaceutical applications, which are often prepared at elevated temperatures. Polymorph B can be obtained as a fine powder with a particle size that may range from 0.2 μm to 500 μm.

Figure 1:
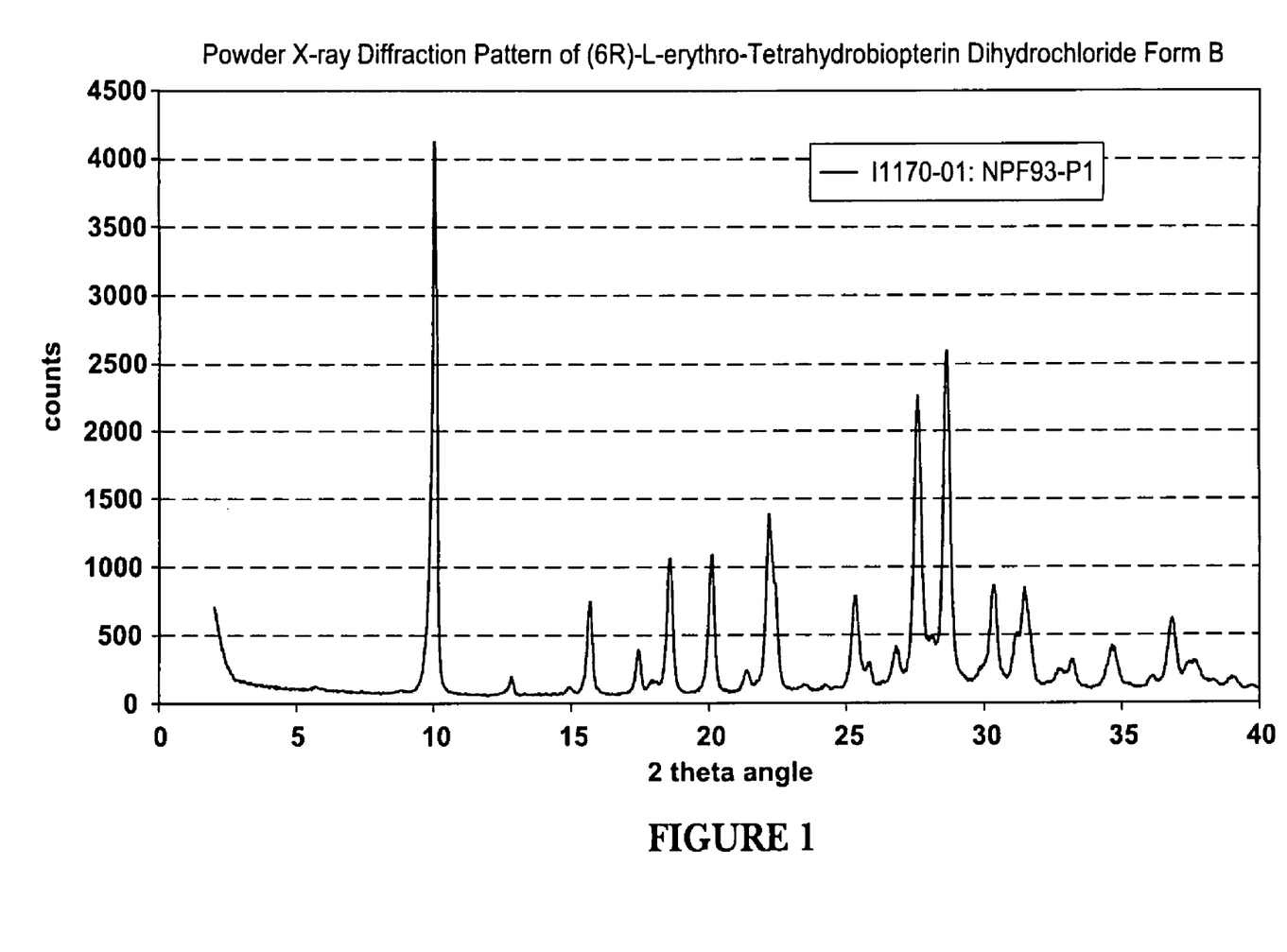
FIG. 1 shows a characteristic X-ray powder diffraction pattern for crystalline polymorph B of (6R)-5,6,7,8-tetrahydrobiopterin dihydrochloride.

Form B exhibits an X-ray powder diffraction pattern, expressed in d-values (Å) at: 8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), 2.44 (w). FIG. 1 is a graph of the characteristic X-ray diffraction pattern exhibited by form B of (6R)-L-erythro-tetrahydrobiopterin dihydrochloride. As used herein, the following the abbreviations in brackets mean: (vs)=very strong intensity; (s)=strong intensity; (m)=medium intensity; (w)=weak intensity; and (vw)=very weak intensity.

Form B can be prepared in very large quantities (e.g., 100 kilo scale) and stored over an extended period of time.

All crystal forms (polymorphs, hydrates and solvates), inclusive crystal form B, can be used for the preparation of the most stable polymorph B. Polymorph B may be obtained by phase equilibration of suspensions of amorphous or other forms, in suitable polar and non aqueous solvents.

Other forms of BH4 can be converted into form B by dispersing the other form of BH4 in a solvent at room temperature, stirring the suspension at ambient temperatures for a time sufficient to produce polymorph form B, thereafter isolating crystalline form B and removing the solvent from the isolated form B. Ambient temperatures, as used herein, mean temperatures in a range from 0° C. to 60° C., preferably 15° C. to 40° C. The applied temperature may be changed during treatment and stirring by decreasing the temperature stepwise or continuously. Suitable solvents for the conversion of other forms to form B include but are not limited to, methanol, ethanol, isopropanol, other C3- and C4-alcohols, acetic acid, acetonitrile, tetrahydrofurane, methyl-t-butyl ether, 1,4-dioxane, ethyl acetate, isopropyl acetate, other C3-C6-acetates, methyl ethyl ketone and other methyl-C3-C5 alkyl-ketones. The time to complete phase equilibration may be up to 30 hours and preferably up to 20 hours or less than 20 hours.

Polymorph B may also be obtained by crystallisation from solvent mixtures containing up to about 5% water, especially from mixtures of ethanol, acetic acid and water. It has been found that polymorph form B of (6R)-L-erythro-tetrahydrobiopterin dihydrochloride can be prepared by dissolution, optionally at elevated temperatures, preferably of a solid lower energy form than form B or of form B of (6R)-L-erythro-tetrahydrobiopterin dihydrochloride in a solvent mixture comprising ethanol, acetic acid and water, addition of seeds to the solution, cooling the obtained suspension and isolation of the formed crystals. Dissolution may be carried out at room temperature or up to 70° C., preferably up to 50° C. There may be used the final solvent mixture for dissolution or the starting material may be first dissolved in water and the other solvents may than be added both or one after the other solvent. The composition of the solvent mixture may comprise a volume ratio of water:acetic acid:tetrahydrofuran of 1:3:2 to 1:9:4 and preferably 1:5:4. The solution is preferably stirred. Cooling may mean temperatures down to −40° C. to 0° C., preferably down to 10° C. to 30° C. Suitable seeds are polymorph form B from another batch or crystals having a similar or identical morphology. After isolation, the crystalline form B can be washed with a non-solvent such as acetone or tetrahydrofurane and dried in usual manner.

Polymorph B may also be obtained by crystallization from aqueous solutions through the addition of non-solvents such as methanol, ethanol and acetic acid. The crystallisation and isolation procedure can be advantageously carried out at room temperature without cooling the solution. This process is therefore very suitable to be carried out at an industrial scale.

In one embodiment of the compositions and methods described herein, a composition including polymorph form B of (6R)-L-erythro-tetrahydrobiopterin dihydrochloride is prepared by dissolution of a solid form other than form B or of form B of (6R)-L-erythro-tetrahydrobiopterin dihydrochloride in water at ambient temperatures, adding a non-solvent in an amount sufficient to form a suspension, optionally stirring the suspension for a certain time, and thereafter isolation of the formed crystals. The composition is further modified into a pharmaceutical composition as described below.

The concentration of (6R)-L-erythro-tetrahydrobiopterin dihydrochloride in the aqueous solution may be from 10 to 80 percent by weight, more preferably from 20 to 60 percent by weight, by reference to the solution. Preferred non-solvents (i.e., solvents useful in preparing suspensions of BH4) are methanol, ethanol and acetic acid. The non-solvent may be added to the aqueous solution. More preferably, the aqueous solution is added to the non-solvent. The stirring time after formation of the suspension may be up to 30 hours and preferably up to 20 hours or less than 20 hours. Isolation by filtration and drying is carried out in known manner as described above.

Polymorph form B is a very stable crystalline form, that can be easily filtered off, dried and ground to particle sizes desired for pharmaceutical formulations. These outstanding properties renders polymorph form B especially feasible for pharmaceutical application.

III. STABLE PHARMACEUTICAL FORMULATIONS

Pharmaceutical formulations may initially include a stable crystalline form of tetrahydrobiopterin, or a precursor or derivative or analog thereof, with a pharmaceutically acceptable carrier. The stable formulation of the invention preferably contains one or more of the following additional ingredients that improve the stability or other characteristics of the formulation: binder, disintegration agent, acidic antioxidant, or lubricant or combinations thereof. Preferably a stable tablet formulation includes a binder and disintegration agent, optionally with an acidic antioxidant, and optionally further including a lubricant.

The initial amount of a crystalline polymorph of (6R)-L-erythro-tetrahydrobiopterin used to prepare the formulation may be, for example, in the range of about 30 wt % to about 40 wt % of the formulation, or in the range of about 32 wt % to about 35 wt %, or at about 33 wt %.

Binders assist in maintaining the tablet formulation. In some cases, anhydrous binders are used to preserve the anhydrous state of polymorph B. In some cases, the binder may act as a drying agent. Exemplary binders include anhydrous dibasic calcium phosphate and its monohydrate.

Exemplary concentrations of the binder in a stable tablet formulation of the present invention are between about 1 wt % to about 5 wt %. Particularly contemplated concentrations are between about 1.5 and 3 wt %. Also contemplated are concentrations of binder of at least about 1.6, 1.7, 1.8, 1.9, 2.0, 2.1, 2.2, 2.3, 2.4, 2.5, 2.6, 2.7, 2.8, 2.9, and 3.0 wt %, or concentrations up to about 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0 wt %. The weight ratio of binder to tetrahydrobiopterin in a stable tablet formulation of the present invention is, for example, in the range of about 1:10 to about 1:20. Also contemplated are weight ratios of about 1:10.25, 1:10.5, 1:10.75, 1:11, 1:11.25, 1:11.5, 1:11.75, 1:12, 1:12.25, 1:12.5, 1:12.75, 1:13, 1:13.25, 1:13.5, 1:13.75, 1:14, 1:14.25, 1:14.5, 1:14.75, 1:15, 1:15.25, 1:15.5, 1:15.75, 1:16, 1:16.25, 1:16.5, 1:16.75, 1:17, 1:17.25, 1:17.5, 1:17.75, 1:18, 1:18.25, 1:18.5, 1:18.75, 1:19, 1:19.25, 1:19.5, and 1:19.75.

Disintegration agents assist in rapid disintegration of solid formulations by absorbing water and expanding. Exemplary disintegration agents include polyvinylpyrrolidone (PVP, e.g. sold under the name POVIDONE), a cross-linked form of povidone (CPVP, e.g. sold under the name CROSPOVIDONE), a cross-linked form of sodium carboxymethylcellulose (NaCMC, e.g. sold under the name AC-DI-SOL), other modified celluloses, and modified starch. Tablets formulated with CPVP exhibited much more rapid disintegration than tablets formulated with PVP.

Exemplary concentrations of the disintegration agent in a stable table formulation of the present invention are between about 1 wt % to about 20 wt %. Particularly contemplated concentrations are between about 3 wt % and about 10 wt %. Also contemplated are concentrations of disintegration of at least about 1.1, 1.2, 1.3, 1.4, 1.5, 1.6, 1.7, 1.6, 1.9, 2.0, 2.1, 2.2, 2.3, 2.4, 2.5, 2.6, 2.7, 2.6, 2.9, and 3.0 wt %, or concentrations up to about 4.0, 4.1, 4.2, 4.3, 4.4, 4.5, 4.6, 4.7, 4.8, 4.9, 5.0, 5.2, 5.4, 5.6, 5.7, 5.8, 6.0, 6.25, 6.5, 6.75, 8.0, 8.25, 8.5, 8.75, 9.0, 9.25, 9.5, 9.75, and 10.0 wt %. The weight ratio of disintegration agent to tetrahydrobiopterin in a stable tablet formulation of the present invention is, for example, in the range of about 1:5 to about 1:10. Also contemplated are weight ratios of about 1:5.25, 1:5.5, 1:5.75, 1:6.0, 1:6.25, 1:6.5, 1:6.75, 1:7.0, 1:7.25, 1:7.5, 1:7.75, 1:8.0, 1:8.25, 1:8.5, 1:8.75, 1:9.0, 1:9.25, 1:9.5, and 1:9.75.

Antioxidants may be included and help stabilize the tetrahydrobiopterin product, especially after dissolution. Low pH aqueous solutions of API are more stable than are solutions at high pH. Exemplary acidic antioxidants include ascorbic acid, fatty acid esters of ascorbic acid such as ascorbyl palmitate and ascorbyl stearate, and salts of ascorbic acid such as sodium, calcium, or potassium ascorbate. Non-acidic antioxidants may also be used in the stable tablet formulations. Nonlimiting examples of non-acidic antioxidants include beta-carotene, alpha-tocopherol. Acidic additives may be added to enhance stability of the tablet formulation, including citric acid or malic acid.

Exemplary concentrations of the antioxidant in a stable table formulation of the present invention are between about 1 wt % and about 3 wt %. Particularly contemplated concentrations are at least about 1.1, 1.2, 1.3, 1.4, 1.5, 1.6, 1.7, 1.8, 1.9, and 2.0 wt %, or concentrations up to about 2.1, 2.2, 2.3, 2.4, 2.5, 2.6, 2.7, 2.8, 2.9, and 3.0 wt %. The weight ratio of antioxidant to tetrahydrobiopterin in a stable tablet formulation of the present invention is, for example, in the range of about 1:5 to 1:30. Also contemplated are weight ratios of about 1:5.5, 1:6, 1:6.5, 1:7, 1:7.5, 1:8, 1:8.5, 1:9, 1:9.5, 1:10, 1:10.5, 1:11, 1:11.5, 1:12, 1:12.5, 1:13, 1:13.5, 1:14, 1:14.5, 1:15, 1:15.5, 1:16, 1:16.5, 1:17, 1:17.5, 1:18, 1:18.5, 1:19, 1:19.5, 1:20, 1:20.5, 1:21, 1:21.5, 1:22, 1:22.5, 1:23, 1:23.5, 1:24, 1:24.5, 1:25, 1:25.5, 1:26, 1:26.5, 1:27, 1:27.5, 1:28, 1:28.5, 1:29, and 1:29.5.

In Schirk's Laboratory tablets, ascorbic acid is present at a ratio of 1:1 to BH4. In contrast, the concentration of ascorbic acid in the stable formulations of the invention is far lower, e.g. a weight ratio (mg/mg) of 1:20 of ascorbic acid to BH4. Thus, the invention also contemplates formulations comprising ascorbic acid at a ratio to BH4 of less than 1:1, e.g. 1:2, 1:3, 1:4, 1:5, 1:6, 1:7, 1:8, 1:9, 1:10, 1:11, 1:12, 1:13, 1:14, 1:15, 1:16, 1:17, 1:18 or 1:19, preferably a ratio of less than 1:10.

Lubricants improve stability, hardness and uniformity of solid formulations. Exemplary lubricants include stearyl fumarate and magnesium stearate.

Exemplary concentrations of the lubricant in a stable tablet formulation of the present invention are between about 0.1 wt % and about 2 wt %. Particularly contemplated concentrations are between about 0.5 and 1 wt %. Also contemplated are concentrations of lubricant of at least about 0.1, 0.2, 0.3, 0.4, 0.5, 0.6, 0.7, 0.8, 0.9, and 1.0 wt %, or concentrations up to about 1.1, 1.2, 1.3, 1.4, 1.5, 1.6, 1.7, 1.8, 1.9, and 2.0 wt %. The weight ratio of lubricant to tetrahydrobiopterin in a stable tablet formulation of the present invention is, for example, in the range of about 1:25 to 1:65. Also contemplated are weight ratios of about 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, and 1:65.

The stable solid formulation may optionally include other therapeutic agents suitable for the condition to be treated, e.g. folates, including folate precursors, folic acids, or folate derivatives; and/or arginine; and/or vitamins, such as vitamin C and/or vitamin B 2 (riboflavin) and/or vitamin B12; and/or neurotransmitter precursors such as L-dopa or carbidopa; and/or 5-hydroxytryptophan.

Exemplary folates, including folate precursors, folic acids, or folate derivatives, are disclosed in U.S. Pat. Nos. 6,011,040 and 6,544,994, both of which are incorporated herein by reference, and include folic acid (pteroylmonoglutamate), dihydrofolic acid, tetrahydrofolic acid, 5-methyltetrahydrofolic acid, 5,10-methylenetetrahydrofolic acid, 5,10-methenyltetrahydrofolic acid, 5,10-formiminotetrahydrofolic acid, 5-formyltetrahydrofolic acid (leucovorin), 10-formyltetrahydrofolic acid, 10-methyltetrahydrofolic acid, one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one carbon units at various levels of oxidation, or pharmaceutically compatible salts thereof, or a combination of two or more thereof. Exemplary tetrahydrofolates include 5-formyl-(6S)-tetrahydrofolic acid, 5-methyl-(6S)-tetrahydrofolic acid, 5,10-methylene-(6R)-tetrahydrofolic acid, 5,10-methenyl-(6R)-tetrahydrofolic acid, 10-formyl-(6R)-tetrahydrofolic acid, 5-formimino-(6S)-tetrahydrofolic acid or (6S)-tetrahydrofolic acid, and pharmaceutically acceptable salts thereof. Exemplary salts include sodium, potassium, calcium or ammonium salts.

Exemplary relative weight ratios of BH4 to folates to arginine may be from about 1:10:10 to about 10:1:1.

Optionally the stable formulations of the invention can also comprise other excipients such as mannitol, hydroxylpropyl cellulose, microcrystalline cellulose, or other non-reducing sugars such as sucrose, trehalose, melezitose, planteose, and raffinose. Reducing sugars may react with BH4.

Pharmaceutically acceptable ingredients for manufacturing solid formulations for oral administration may be incorporated, for example, by admixing the components and optionally finely dividing them, and then filling capsules, composed for example from hard or soft gelatin, compressing tablets, pills or troches. Coatings may be applied after compression to form pills.

Pharmaceutically acceptable ingredients are well known for the various types of formulation and may be for example binders such as natural or synthetic polymers, excipients, lubricants, surfactants, sweetening and flavouring agents, coating materials, preservatives, dyes, thickeners, adjuvants, antimicrobial agents, antioxidants and carriers for the various formulation types. Nonlimiting examples of binders useful in a composition described herein include gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan.

Nonlimiting examples of excipients useful in a composition described herein include phosphates such as dicalcium phosphate. Nonlimiting examples of lubricants use in a composition described herein include natural or synthetic oils, fats, waxes, or fatty acid salts such as magnesium stearate.

Surfactants for use in a composition described herein can be anionic, anionic, amphoteric or neutral. Nonlimiting examples of surfactants useful in a composition described herein include lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, I-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Nonlimiting examples of sweetening agents useful in a composition described herein include sucrose, fructose, lactose or aspartame. Nonlimiting examples of flavoring agents for use in a composition described herein include peppermint, oil of wintergreen or fruit flavors such as cherry or orange flavor. Nonlimiting examples of coating materials for use in a composition described herein include gelatin, wax, shellac, sugar or other biological degradable polymers. Nonlimiting examples of preservatives for use in a composition described herein include methyl or propylparabens, sorbic acid, chlorobutanol, phenol and thimerosal.

The polymorph described herein may also be formulated as effervescent tablet or powder, which disintegrate in an aqueous environment to provide a drinking solution. Slow release formulations may also be prepared from the polymorph described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The BH4 used in a composition described herein is preferably formulated as a dihydrochloride salt, however, it is contemplated that other salt forms of BH4 possess the desired biological activity, and consequently, other salt forms of BH4 can be used. Specifically, BH4 salts with inorganic or organic acids are preferred. Nonlimiting examples of alternative BH4 salts forms includes BH4 salts of acetic acid, citric acid, oxalic acid, tartaric acid, fumaric acid, and mandelic acid.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'dibenzylethylenediamine, chloroprocaine, choline, diethanolamine, dicyclohexylamine, ethylenediamine, N methylglucamine, and procaine.

Pharmaceutically acceptable acid addition salts include inorganic or organic acid salts. Examples of suitable acid salts include the hydrochlorides, acetates, citrates, salicylates, nitrates, phosphates. Other suitable pharmaceutically acceptable salts are well known to those skilled in the art and include, for example, acetic, citric, oxalic, tartaric, or mandelic acids, hydrochloric acid, hydrobromic acid, sulfuric acid or phosphoric acid; with organic carboxylic, sulfonic, sulfo or phospho acids or N substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4 aminosalicylic acid, 2 phenoxybenzoic acid, 2 acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2 hydroxyethanesulfonic acid, ethane 1,2 disulfonic acid, benzenesulfonic acid, 4 methylbenzenesulfoc acid, naphthalene 2 sulfonic acid, naphthalene 1,5 disulfonic acid, 2 or 3 phosphoglycerate, glucose 6 phosphate, N cyclohexylsulfamic acid (with the formation of cyclamates), or with other acid organic compounds, such as ascorbic acid.

The stable formulations of the invention may be provided, e.g. as tablets or pills or capsules in HDPE bottles provided with a desiccant capsule or pouch; or in foil-on-foil blister packaging, or in blister packaging comprising see-through polymer film, if commercially desirable.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the therapeutic compositions, its use in therapeutic compositions is contemplated. Supplementary active ingredients also can be incorporated into the compositions.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

IV. TREATMENT METHODS USING STABLE FORMULATIONS

The stable formulations of the invention may be used for treatment of conditions associated with elevated phenylalanine levels or decreased tyrosine or tryptophan levels, which may be caused, for example, by reduced phenylalanine hydroxylase, tyrosine hydroxylase, or tryptophan hydroxylase activity. Conditions associated with elevated phenylalanine levels specifically include phenylketonuria, both mild and classic, and hyperphenylalaninemia as described herein, and exemplary patient populations include the patient subgroups described herein as well as any other patient exhibiting phenylalanine levels above normal. Conditions associated with decreased tyrosine or tryptophan levels include neurotransmitter deficiency, neurological and psychiatric disorders such as Parkinson's, dystonia, spinocerebellar degeneration, pain, fatigue, depression, other affective disorders and schizophrenia.

The stable formulations may also be used for treating patients suffering from BH4 deficiency, e.g., due to a defect in the pathway for its synthesis, including but not limited to dopa-responsive dystonia (DRD), sepiapterin reductase (SR) deficiency, or dihydropteridine reductase (DHPR) deficiency.

Suitable subjects for treatment with the stable formulations of the invention include subjects with an elevated plasma Phe concentration in the absence of the therapeutic, e.g. greater than 1800 μM/L, or greater than 1600 μM, greater than 1400 μM, greater than 1200 μM, greater than 1000 μM, greater than 800 μM, or greater than 600 μM, greater than 420 μM, greater than 300 μM, greater than 200 μM, or greater than 180 μM. Mild PKU is generally classified as plasma Phe concentrations of up to 600 μM/L, moderate PKU as plasma Phe concentrations of between 600 μM/L to about 1200 μM/L and classic or severe PKU as plasma Phe concentrations that are greater than 1200 μM/L. Preferably treatment with the stable formulations alone or with protein-restricted diet decreases the plasma phenylalanine concentration of the subject to less than 600 μM, or less than 500 μM, or 360 μM±15 μM or less, or less than 200 μM, or less than 100 μM. Other suitable subjects include subjects diagnosed as having a reduced phenylalanine hydroxylase (PAH) activity. Reduced PAH activity may result from a mutation in the PAH enzyme, for example, a mutation in the catalytic domain of PAH or one or more mutations selected from the group consisting of F39L, L48S, I65T, R68S, A104D, S110C, D129G, E178G, V190A, P211T, R241c, R261Q, A300S, L308F, A313T, K320N, A373T, V388M E390G, A395P, P407S, and Y414C; or subjects that are pregnant females, females of child-bearing age that are contemplating pregnancy, or infants between 0 and 3 years of age, or 0-2, 0-1.5 or 0-1; or subjects diagnosed as unresponsive within 24 hours to a single-dose BH4 loading test or a multiple dose loading test, such as a 4-dose or 7-day loading test. Exemplary patient populations and exemplary BH4 loading tests are described in Int'l. Publication No. WO 2005/049000, incorporated herein by reference in its entirety.

U.S. Pat. Nos. 4,752,573; 4,758,571; 4,774,244; 4,920,122; 5,753,656; 5,922,713; 5,874,433; 5,945,452; 6,274,581; 6,410,535; 6,441,038; 6,544,994; and U.S. Patent Publications US 20020187958; US 20020106645; US 2002/0076782; US 20030032616 (each incorporated herein by reference) each describe methods of administering BH4 compositions for non-PKU treatments. Each of those patents is incorporated herein by reference as providing a general teaching of methods of administering BH4 compositions known to those of skill in the art, that may be adapted for the treatment as described herein.

While individual needs vary, determination of optimal ranges of effective amounts of each component is within the skill of the art. Typical dosages of the BH4 comprise about 1 to about 20 mg/kg body weight per day, which will usually amount to about 5 (1 mg/kg×5 kg body weight) to 3000 mg/day (30 mg/kg×100 kg body weight). While continuous, daily administration is contemplated, for HPA it may be desirable to cease the BH4 therapy when the symptoms of Phe levels are reduced to below a certain threshold level. Of course, the therapy may be reinitiated in the event that Phe levels rise again. Appropriate dosages may be ascertained through the use of established assays for determining blood levels of Phe in conjunction with relevant dose response data.

In preferred embodiments, it is contemplated that the methods of the present invention will provide to a patient in need thereof, a daily dose of between about 10 mg/kg to about 20 mg/kg of BH4. Of course, one skilled in the art may adjust this dose up or down depending on the efficacy being achieved by the administration. The daily dose may be administered in a single dose or alternatively may be administered in multiple doses at conveniently spaced intervals. In exemplary embodiments, the daily dose may be 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg, 24 mg/kg, 26 mg/kg, 28 mg/kg, 30 mg/kg, 32 mg/kg, 34 mg/kg, 36 mg/kg, 38 mg/kg, 40 mg/kg, 42 mg/kg, 44 mg/kg, 46 mg/kg, 48 mg/kg, 50 mg/kg, or more mg/kg.

The invention further contemplates that stable formulations of the invention may be used for treatment of subjects suffering from conditions that would benefit from enhancement of nitric oxide synthase activity and patients suffering from vascular diseases, ischemic or inflammatory diseases, or insulin resistance. The treatment may, for example alleviate a deficiency in nitric oxide synthase activity or may, for example provide an increase in nitric oxide synthase activity over normal levels. It has been suggested that a patient suffering from a deficiency in nitric oxide synthase activity would benefit from co-treatment with folates, including folate precursors, folic acids, or folate derivatives.

Nitric oxide is constitutively produced by vascular endothelial cells where it plays a key physiological role in the regulation of blood pressure and vascular tone. It has been suggested that a deficiency in nitric oxide bioactivity is involved in the pathogenesis of vascular dysfunctions, including coronary artery disease, atherosclerosis of any arteries, including coronary, carotid, cerebral, or peripheral vascular arteries, ischemia-reperfusion injury, hypertension, diabetes, diabetic vasculopathy, cardiovascular disease, peripheral vascular disease, or neurodegenerative conditions stemming from ischemia and/or inflammation, such as stroke, and that such pathogenesis includes damaged endothelium, insufficient oxygen flow to organs and tissues, elevated systemic vascular resistance (high blood pressure), vascular smooth muscle proliferation, progression of vascular stenosis (narrowing) and inflammation. Thus, treatment of any of these conditions is contemplated according to methods of the invention.

It has also been suggested that the enhancement of nitric oxide synthase activity also results in reduction of elevated superoxide levels, increased insulin sensitivity, and reduction in vascular dysfunction associated with insulin resistance, as described in U.S. Pat. No. 6,410,535, incorporated herein by reference. Thus, treatment of diabetes (type I or type II), hyperinsulinemia, or insulin resistance is contemplated according to the invention. Diseases having vascular dysfunction associated with insulin resistance include those caused by insulin resistance or aggravated by insulin resistance, or those for which cure is retarded by insulin resistance, such as hypertension, hyperlipidemia, arteriosclerosis, coronary vasoconstrictive angina, effort angina, cerebrovascular constrictive lesion, cerebrovascular insufficiency, cerebral vasospasm, peripheral circulation disorder, coronary arteriorestenosis following percutaneous transluminal coronary angioplasty (PTCA) or coronary artery bypass grafting (CABG), obesity, insulin-independent diabetes, hyperinsulinemia, lipid metabolism abnormality, coronary arteriosclerotic heart diseases or the like so far as they are associated with insulin resistance. It is contemplated that when administered to patients with these diseases, BH4 can prevent or treat these diseases by activating the functions of NOS, increasing NO production and suppressing the production of active oxygen species to improve disorders of vascular endothelial cells.

It is understood that the suitable dose of a composition according to the present invention will depend upon the age, health and weight of the recipient, kind of concurrent treatment, if any, frequency of treatment, and the nature of the effect desired (i.e., the amount of decrease in plasma Phe concentration desired). The frequency of dosing also is dependent on pharmacodynamic effects on Phe levels. If the effect lasts for 24 hours from a single dose. However, the most preferred dosage can be tailored to the individual subject, as is understood and determinable by one of skill in the art, without undue experimentation. This typically involves adjustment of a standard dose, e.g., reduction of the dose if the patient has a low body weight.

The frequency of BH4 dosing will depend on the pharmacokinetic parameters of the agent and the routes of administration. The optimal pharmaceutical formulation will be determined by one of skill in the art depending on the route of administration and the desired dosage. See for example Remington's Pharmaceutical Sciences, 18th Ed. (1990, Mack Publ. Co, Easton Pa. 18042) pp 1435 1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

V. COMBINATION THERAPY

Certain methods of the invention involve the combined use of the stable formulations of the invention and one or more other therapeutic agents.

In such combination therapy, administration of the stable formulations of the invention may be concurrent with or may precede or follow the administration of the second therapeutic agent, e.g. by intervals ranging from minutes to hours, so long as both agents are able to exert their therapeutic effect at overlapping time periods. Thus, the invention contemplates the stable formulations of the invention for use with a second therapeutic agent. The invention also contemplates use of a second therapeutic agent in preparation of a medicament for administration with the stable tetrahydrobiopterin, precursor, derivative or analog formulations of the invention.

Tetrahydrobiopterin therapy may be combined with dietary protein restriction to effect a therapeutic outcome in patients with various forms of HPA. For example, one could administer to the subject the BH4 composition and a low-phenylalanine medical protein composition in a combined amount effective to produce the desired therapeutic outcome (i.e., a lowering of plasma Phe concentration and/or the ability to tolerate greater amounts of Phe/protein intake without producing a concomitant increase in plasma Phe concentrations). This process may involve administering the BH4 composition and the dietary protein therapeutic composition at the same time. This may be achieved by administering a single composition or pharmacological protein formulation that includes all of the dietary protein requirements and also includes the BH4 within said protein formulation. Alternatively, the dietary protein (supplement or normal protein meal) is taken at about the same time as a pharmacological formulation (tablet, injection or drink) of BH4.

In other alternatives, the BH4 treatment may precede or follow the dietary protein therapy by intervals ranging from minutes to hours. In embodiments where the protein and the BH4 compositions are administered separately, one would generally ensure that a significant period of time did not expire between the time of each delivery, such that the BH4 will still be able to exert an advantageously effect on the patient. In such instances, it is contemplated that one would administer the BH4 within about 2-6 hours (before or after) of the dietary protein intake, with a delay time of only about 1 hour being most preferred. In certain embodiments, it is contemplated that the BH4 therapy will be a continuous therapy where a daily dose of BH4 is administered to the patient indefinitely. In other situations, e.g., in pregnant women having only the milder forms of PKU and HPA, it may be that the BH4 therapy is only continued for as long as the woman is pregnant and/or breast feeding.

Further, in addition to therapies based solely on the delivery of BH4 and dietary protein regulation, the methods of the present invention also contemplate combination therapy with a third composition that specifically targets one or more of the symptoms of HPA. For example, it is known that the deficit in tyrosine caused by HPA results in a deficiency in neurotransmitters dopamine and serotonin. Thus, in the context of the present invention, it is contemplated that BH4 and dietary protein based methods could be further combined with administration of L-dopa, carbidopa and 5-hydroxytryptophan neurotransmitters to correct the defects that result from decreased amounts of tyrosine in the diet.

In addition, gene therapy with both PAH (Christensen et al., *Mol. Gent. And Metabol.* 76: 313-318, 2002; Christensen et al., Gene Therapy, 7:1971-1978, 2000) and phenylalanine ammonia-lyase (PAL Liu et al., *Arts. Cells. Blood. Subs and Immob. Biotech*. 30(4)243-257, 2002) has been contemplated by those of skill in the art. Such gene therapy techniques could be used in combination with the combined BH4/dietary protein restriction based therapies of the invention. In further combination therapies, it is contemplated that phenylase may be provided as an injectable enzyme to destroy lower Phe concentrations in the patient. As the administration of phenylase would not generate tyrosine (unlike administration of PAH), such treatment will still result in tyrosine being an essential amino acid for such patients. Therefore dietary supplementation with tyrosine may be desirable for patients receiving phenylase in combination with the BH4 therapy.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of Stabilized Crystallized Form of BH4

Int'l. Publication No. WO 2005/065018, incorporated herein by reference in its entirety, describes X ray and Raman spectra studies to characterize the polymorphs, including hydrates or solvates, of BH4, as well as exemplary crystallization conditions under which the polymorphs can be prepared. Int'l Publication No. WO 2005/049000, incorporated herein by reference in its entirety, describes various patient populations for which BH4 treatment is suitable and describes methods for treating such subjects with BH4. Int'l Publication No. WO2005/049614 incorporated herein by reference in its entirety, describe methods of synthesizing BH4.

The references cited herein throughout, to the extent that they provide exemplary procedural or other details supplementary to those set forth herein, are all specifically incorporated herein by reference.

Example 2

Stable Tablet Formulation of Tetrahydrobiopterin

Three tablet formulations were prepared by mixing the ingredients shown in Table I as described in detail below.

TABLE I

| Ingredient | Formulation I (wt %) | Formulation II (wt %) | Formulation III (wt %) |
| --- | --- | --- | --- |
| 6R-L-erythro-5,6,7,8-tetrahydrobiopterin dihydrochloride salt, polymorph B (Active Ingredient) | 33.33 | 33.33 | 33.33 |
| D-Mannitol (Taste Masking) | 57.56 | 57.56 | 57.56 |
| Dibasic Calcium Phosphate, Anhydrous (Binder) | 2.18 | 2.18 | 2.18 |
| Hydroxypropyl Cellulose (Disintegrant) | 3.63 | 4.5 | |
| Polyvinylpyrrolidone (Disintegrant) | 0.87 | | 4.50 |
| Ascorbic acid (Stabilizer) | 1.67 | 1.67 | 1.67 |
| Riboflavin (Coloring Agent) | 0.01 | 0.01 | 0.01 |
| Sodium Stearyl Fumarate (Lubricant) | 0.75 | 0.75 | 0.75 |

For each formulation in Table I, twelve kilogram batches were prepared by first charging 4 kg of 6R-L-erythro-5,6,7,8-tetrahydrobiopterin dihydrochloride salt (SAPROPTERIN Hydrochloride, available from Daiichi Suntory Pharma Co., Ltd., Japan to a blender and blending the BH4 for 10 minutes at 25 revolutions per minute (RPM). Then 6.91 kg of D-Mannitol (PEARLITOL, available from Roquette America, Inc., Keokuk, Iowa) was added to the blender and the mixture was allowed to blend for an additional 10 minutes at 25 RPM. Then 260 grams of Anhydrous Dibasic Calcium Phosphate (available from Mallinckrodt Baker, Inc., Phillipsburg, N.J.) and (a) in Formulation I, 436 grams of Hydroxypropyl Cellulose and 104 grams were added to the blender, (b) in Formulation II 540 grams of Hydroxypropyl Cellulose was added to the blender; (c) in Formulation III, 540 grams of Polyvinylpyrrolidone (KOLLIDON CL, available from BASF Corporation, Florham Park, N.J.) were added to the blender, and the mixture was allowed to blend for an additional 10 minutes at 25 RPM. To the bender 200 grams of Ascorbic Acid and 120 grams of Riboflavin were added to the blender and the mixture was allowed to blend for 3 minutes at 25 RPM. The Sodium Stearyl Fumarate lubricant (PRUV, available from Penwest Pharmaceuticals Co., Danbury, Conn.) was filtered through a 25 mesh stainless steel screen and into a bag, and the blender was then charged with 9 kg of the screened Sodium Stearyl Fumarate, and the resulting mixture was allowed to blend for 5 minutes at 25 RPM.

The blended mixture of each formulation were then removed from the blender, and three samples of each formulation were collected for the preparation of a 150 mg, a 300 mg, and a 600 mg tablets. For each formulation, the tablet samples (150 mg, 300 mg, and 600 mg) were placed in a tablet press (available from Jenn-Chiang Mahinery Co., Ltd., Taiwan, R.O.C.) wherein the parameters of the tablet press were set to provide tablets with a thickness in the range of 4.5 to 5.5 millimeters, and a target hardness of 7 KP.

The resulting tablets were then analyzed to determine the stability of the formulations. The stability of the formulations was studied for a change in appearance over time by a visual inspection at different intervals, for disintegration of the formulation utilizing the United States Pharmacopeia recommendations no. 701, and for a chemical change by assaying the components of the formulations. The results of the stability tests are summarized below in Table II.

amounts shown below in Table III using the following dry tableting process. Tablets containing other desired amounts of tetrhydrobiopterin can be prepared in a similar manner.

The 6R-erythro-5,6,7,8-tetrahydrobiopterin and D-Mannitol were hand screened with a 20 mesh screen (designed to filter out particles greater than ~850 μm in size) and placed in a blender. The mixture was blended for 10 minutes at 21 RPM. Next, the Anhydrous Dibasic Calcium Phosphate and CROSPOVIDONE were hand screened with a 20 mesh screen and blended with the BH4 and D-Mannitol for 10 minutes at 21 RPM. The Ascorbic Acid and Riboflavin were added to the blender after hand screening with a 20 mesh screen, and the resulting mixture blended for 10 minutes at 21 RPM. Next, the Sodium Stearyl Fumarate was added to the blender after hand screening with a 40 mesh screen, and

TABLE II

| Form. | Test | Initial | 2 weeks | 4 weeks | 8 weeks |
|---|---|---|---|---|---|
| I | Appearance | Off white, round Tablets | Dark yellow spots (diameter 1-2 mm) on the off white tablets | Dark yellow spots (diameter 1-2 mm) on the off white tablets | Dark yellow spots (diameter 1-2 mm) on the off white tablet |
| | Disintegration | 5 min 20 sec | 5 min 40 sec | 8 min 4 sec | — |
| | Chemical Assay | 97.10% | 97.90% | 98.2 | 100.7 |
| II | Appearance | Off white round Tablets | Broken chip on some tablets. Light yellow spots (diameter 1-2 mm) on the off white round tablets. | Broken chip on some tablets. Light yellow spots (diameter 1-2 mm) on the off white round tablets | Broken chip on some tablets. Light brown spots (diameter 1-2 mm) on the dark brown tablets |
| | Disintegration | 4 min 10 sec | 4 min 38 sec | 6 min 52 sec | — |
| | Chemical Assay | 102.70% | 100.00% | 100.2 | 97.4 |
| III | Appearance | Color is off white | Rough surface, and color is light yellow | Rough surface, and color is light yellow | Rough surface, and color is yellow |
| | Disintegration | 1 min 52 sec | 35 sec | 58 sec | — |
| | Chemical Assay | 100.20% | 102.90% | 97.4 | 99.8 |

The stability tests show that tablet Formulation III is more stable that the other formulations of BH4. Each of the pharmaceutical preparations are useful formulations for the delivery of BH4. Formulation III exhibited better stability than Formulations I and II. Thus, in one preferred embodiment, the stabilized tablet formulation comprises an optimal disintegration agent, for example, crossprovidone or a disintegration agent more similar to polyvinylpyrrolidone than hydroxypropylcellulose. The preferred formulation is Formulation III. Other suitable tablet formulations may include at least ascorbic acid at a concentration of at least 0.01% weight, or at least 0.05% weight or at least 0.1% weight.

Example 3

Three hundred mg tablets containing 100 mg tetrahydrobiopterin are prepared using the desired initial amount of polymorph B and mixing with other ingredients in the relative blended for 5 minutes at 21 RPM. The blended mixture was then discharged into a bag and tested for uniformity, before being pressed into tablets.

TABLE III

| Ingredient | (wt %) | (mg) |
|---|---|---|
| 6R-L-erythro-5,6,7,8-tetrahydrobiopterin dihydrochloride salt (Active Ingredient) | 33.33 | 100.0 |
| D-Mannitol (Taste Masking) | 57.56 | 172.68 |
| Dibasic Calcium Phosphate, Anhydrous (Binder) | 2.18 | 6.54 |
| CROSPOVIDONE (Disintegration Agent) | 4.50 | 13.50 |
| Ascorbic acid (Acidic Antioxidant) | 1.67 | 5.00 |
| Riboflavin | 0.01 | 0.03 |

TABLE III-continued

| Ingredient | (wt %) | (mg) |
|---|---|---|
| (Coloring Agent) | | |
| Stearyl Fumarate | 0.75 | 2.25 |
| (Lubricant) | | |

The tablets were packaged either in foil blister-packs, or in HDPE bottles in quantities of 45-tablets per bottle. Each type of packaged tablets were divided into two batches. One batch was stored at room temperature, 25±2° C., and 60±5% relative humidity. The other batch was stored under accelerated testing conditions, at 40±2° C. and 75±5% relative humidity. At regular intervals, tablets were removed from storage and tested for retention of the active pharmaceutical ingredient, 6R-L-erythro-5,6,7,8-tetrahydrobiopterin. Exemplary results for the 300 mg tablets are shown below in Tables IV, V, VI and VII. After six months storage under room temperature or accelerated testing conditions, each of the four batches showed retention of at least 99% of the original amount of 6R-L-erythro-5,6,7,8-tetrahydrobiopterin by HPLC assay, loss on drying of less than 1%, and rapid disintegration in 3 minutes or less.

TABLE IV

SAPROPTERIN DIHYDROCHLORIDE DRUG PRODUCT
(300-MG TABLET, FOIL BLISTER-PACK)
STORAGE CONDITIONS: 25 ± 2° C./60 ± 5% RH

| | | Time Point (months) | | | | |
|---|---|---|---|---|---|---|
| Test/Assay | Stability Specification | 0 | 1 | 3 | 6 | 9 |
| Appearance by Visual Inspection | White to light yellow compressed tablets | Conforms | Conforms | Conforms | Conforms | Conforms |
| Loss on Drying | Report Result | 0.3% | 0.3% | 0.9% | 0.7% | 0.9% |
| Disintegration | ≦3 minutes | 1 min. 30 sec. | 2 min. 7 sec. | 2 min. 2 sec. | 2 min. 35 sec. | 1 min. 48 sec. |
| HPLC Assay | 90-110% | 101% | 100% | 100% | 100% | 101% |
| HPLC for Related Substances | ≦0.1% individual unidentified | 0.05% | 0.04% (RRT 1.28) | 0.05% (RRT 0.72) 0.08% (RRT 0.83) 0.05% (RRT 1.32) | 0.09% (RRT 0.81) 0.04% (RRT 0.83) 0.06% (RRT 1.24) | 0.03% (RRT 0.69) 0.01% (RRT 0.73) 0.07% (RRT 0.81) 0.03% (RRT 0.83) 0.02% (RRT 1.21) 0.04% (RRT 1.44) |
| | ≦0.5% total unidentified | 0.05% | 0.04% | 0.18% | 0.22% | 0.20% |
| | ≦2.0% total related substances | 0.05% | 0.04% | 0.18% | 0.22% | 0.20% |

ND = None detected

TABLE V

SAPROPTERIN DIHYDROCHLORIDE DRUG PRODUCT
(300-MG TABLET, FOIL BLISTER-PACK)
STORAGE CONDITIONS: 40 ± 2° C./75 ± 5% RH

| | | Time Point (months) | | | |
|---|---|---|---|---|---|
| Test/Assay | Stability Specification | 0 | 1 | 3 | 6 |
| Appearance by Visual Inspection | White to light yellow compressed tablets | Conforms | Conforms | Conforms | Conforms |
| Loss on Drying | Report Result | 0.3% | 0.3% | 0.8% | 0.7% |
| Disintegration | ≦3 minutes | 1 min. 30 sec. | 2 min. 16 sec. | 2 min. 47 sec. | 2 min. 11 sec. |
| HPLC Assay | 90-110% | 101% | 100% | 101% | 99% |
| HPLC for Related Substances | ≦0.1% individual unidentified | 0.05% | 0.04% (RRT 1.28) | 0.06% (RRT 0.64) 0.07% (RRT 0.72) 0.04% (RRT 0.83) 0.06% (RRT 1.31) | 0.07% (RRT 0.74) 0.15% (RRT 0.83) 0.04% (RRT 0.83) 0.06% (RRT 1.24) |

TABLE V-continued

SAPROPTERIN DIHYDROCHLORIDE DRUG PRODUCT
(300-MG TABLET, FOIL BLISTER-PACK)
STORAGE CONDITIONS: 40 ± 2° C./75 ± 5% RH

| Test/Assay | Stability Specification | Time Point (months) | | | |
|---|---|---|---|---|---|
| | | 0 | 1 | 3 | 6 |
| | ≦0.5% total unidentified | 0.05% | 0.04% | 0.23% | 0.32% |
| | ≦2.0% total related substances | 0.05% | 0.04% | 0.23% | 0.32% |

ND = None detected

TABLE VI

SAPROPTERIN DIHYDROCHLORIDE DRUG PRODUCT
(300-MG TABLET, 45 TABLET BOTTLES)
STORAGE CONDITIONS: 25 ± 2° C./60 ± 5% RH

| Test/Assay | Stability Specification | Time point (months) | | |
|---|---|---|---|---|
| | | 0 | 3 | 6 |
| Appearance by Visual Inspection | White to light yellow compressed tablets | Conforms | Conforms | Conforms |
| Loss on Drying | Report Result | 0.7% | 0.8% | 1.1% |
| Disintegration | ≦3 minutes | 2 min 57 sec | 2 min 3 sec | 2 min 50 sec |
| HPLC Assay | 90-110% | 102% | NT | 103% |
| HPLC for Related Substances | ≦0.1% individual unidentified | 0.06% | NT | 0.08% (RRT 0.56) 0.04% (RRT 0.61) 0.05% (RRT 0.65) 0.04% (RRT 0.81) |
| | ≦0.5% total unidentified | 0.15% | NT | 0.21% |
| | ≦2.0% total related substances | 0.15% | NT | 0.21% |
| | Report Result (mg/tablet) | 5 | NT | 5 |
| Total Aerobic Microbial Count | ≦ 1000 cfu/g | <100 cfu/g | NR | NR |
| Test for *Escherichia coli* = absent | | Absent | | |

ND = None detected
NT = Not tested
NR = Not required

TABLE VII

SAPROPTERIN DIHYDROCHLORIDE DRUG PRODUCT
(300-MG TABLET, 45-TABLET BOTTLES)
STORAGE CONDITIONS: 40 ± 2° C./75 ± 5% RH

| Test/Assay | Stability Specification | Time Point (months) | | |
|---|---|---|---|---|
| | | 0 | 3 | 6 |
| Appearance by Visual Inspection | White to light yellow compressed tablets | Conforms | Conforms | Conforms |
| Loss on Drying | Report Result | 0.7% | 1.1% | 1.1% |
| Disintegration | ≦3 minutes | 2 min 57 sec | 2 min 41 sec | 2 min 48 sec |
| HPLC Assay | 90-110% | 102% | NT | 101% |

TABLE VII-continued

SAPROPTERIN DIHYDROCHLORIDE DRUG PRODUCT
(300-MG TABLET, 45-TABLET BOTTLES)
STORAGE CONDITIONS: 40 ± 2° C./75 ± 5% RH

| Test/Assay | Stability Specification | Time Point (months) | | |
|---|---|---|---|---|
| | | 0 | 3 | 6 |
| HPLC for Related Substances | ≦0.1% individual unidentified | 0.06% | NT | 0.13% (RRT 0.56) 0.03% (RRT 0.61) 0.10% (RRT 0.65) 0.04% (RRT 0.81) |
| | ≦0.5% total unidentified | 0.15% | NT | 0.30% |
| | ≦2.0% total related substances | 0.15% | NT | 0.30% |
| | Report Result (mg/tablet) | 5 | NT | 5 |

ND = None detected
NT = Not tested
NR = Not required

What is claimed is:

1. A stable tablet formulation comprising an initial amount of a crystalline polymorph, designated polymorph B, of (6R)-L-erythro-tetrahydrobiopterin dihydrochloride, an antioxidant, and a pharmaceutically acceptable excipient, diluent, or carrier in the form of a tablet,
   wherein the weight ratio of the antioxidant to the (6R)-L-erythro-tetrahydrobiopterin dihydrochloride is about 1:5 to about 1:30;
   wherein after six months in a container at room temperature and about 60% humidity the stable tablet formulation retains at least about 95% of the initial amount of (6R)-L-erythro-tetrahydrobiopterin dihydrochloride,
   and wherein said crystalline polymorph B exhibits an X-ray powder diffraction pattern with the following characteristic peaks expressed in d-values (Å): 8.7 (vs), 5.63 (m), 4.76 (m), 4.40 (m), 4.00 (s), 3.23 (s), and 3.11 (vs).

2. The stable tablet formulation of claim 1, wherein the crystalline polymorph B further exhibits characteristic peaks expressed in d-values (Å): 6.9 (w), 5.07 (m), 4.15 (w), 3.95 (m), 3.52 (m), 3.44 (w), 3.32 (m), 3.17 (w), 3.06 (w), 2.99 (w), 2.96 (w), 2.94 (m), 2.87 (w), 2.84 (s), 2.82 (m), 2.69 (w), 2.59 (w), and 2.44 (w).

3. The stable tablet formulation of claim 1, wherein after six months in a container at room temperature and about 60% humidity the stable tablet formulation retains at least about 98% of the initial amount of (6R)-L-erythro-tetrahydrobiopterin.

4. The stable tablet formulation of claim 1, wherein after nine months in a container at room temperature and about 60% humidity the stable tablet formulation retains at least about 95% of the initial amount of (6R)-L-erythro-tetrahydrobiopterin.

5. The stable tablet formulation of claim 1, wherein after twelve months in a container at room temperature and about 60% humidity the stable tablet formulation retains at least about 95% of the initial amount of (6R)-L-erythro-tetrahydrobiopterin.

6. The stable tablet formulation of claim 1, wherein the initial amount of (6R)-L-erythro-tetrahydrobiopterin is in a range of about 30 wt % to about 40 wt % of the formulation.

7. The stable tablet formulation of claim 1, wherein the initial amount of (6R)-L-erythro-tetrahydrobiopterin in a tablet is selected from the group consisting of 100 mg, 200 mg, and 300 mg.

8. The stable tablet formulation of claim 1, wherein the initial amount of (6R)-L-erythro-tetrahydrobiopterin in a tablet is 400 mg.

9. The stable tablet formulation of claim 1, further comprising a disintegration agent.

10. The stable tablet formulation of claim 9, wherein the disintegration agent is crospovidone.

11. The stable tablet formulation of claim 1, further comprising a lubricant.

12. The stable tablet formulation of claim 11, wherein the lubricant is stearyl fumarate.

13. The stable tablet formulation of claim 12, wherein the stearyl fumarate is sodium stearyl fumarate.

14. The stable tablet formulation of claim 11, wherein the lubricant is present in a range of about 1.0 wt % to about 1.8 wt % of the formulation.

15. The stable tablet formulation of claim 12, further comprising microcrystalline cellulose.

16. The stable tablet formulation of claim 1, comprising an initial amount of the (6R)-L-erythro-tetrahydrobiopterin of about 400 mg, crospovidone in a range of about 3 wt % to about 5 wt % of the formulation, and stearyl fumarate in a range of about 1 wt % to about 1.7 wt % of the formulation.

17. The stable tablet formulation of claim 1, comprising an initial amount of the (6R)-L-erythro-tetrahydrobiopterin in a range of about 32 wt % to about 35 wt % of the formulation, crospovidone in a range of about 3 wt % to about 5 wt % of the formulation, anhydrous dibasic calcium phosphate in a range of about 1.5 wt % to about 3 wt % of the formulation, and stearyl fumarate in a range of about 0.5 wt % to about 2 wt % of the formulation.

18. The stable tablet formulation of claim 1, wherein the antioxidant is an acidic antioxidant.

19. The stable tablet formulation of claim 1, wherein the antioxidant is ascorbic acid.

20. The stable tablet formulation of claim 19, wherein the weight ratio of ascorbic acid to the (6R)-L-erythro-tetrahydrobiopterin dihydrochloride is about 1:20.

* * * * *